United States Patent [19]
Ridinger et al.

[11] Patent Number: 5,800,444
[45] Date of Patent: Sep. 1, 1998

[54] DEVICES FOR REMOVING FIBRIN SHEATHS FROM CATHETERS

[75] Inventors: Mark T. Ridinger; Paul V. Suhocki, both of Durham, N.C.

[73] Assignee: Duke University, Durham, N.C.

[21] Appl. No.: 616,451

[22] Filed: Mar. 15, 1996

Related U.S. Application Data

[62] Division of Ser. No. 417,018, Apr. 5, 1995, Pat. No. 5,556,380.

[51] Int. Cl.$^6$ .......................... A61B 17/24; A61B 17/26
[52] U.S. Cl. .......................... 606/113; 606/110; 606/127
[58] Field of Search .......................... 606/110, 113, 606/114, 127, 106, 108, 222, 224, 139, 144

[56] References Cited

U.S. PATENT DOCUMENTS

| | | |
|---|---|---|
| 798,839 | 9/1905 | Stowe . |
| 1,606,497 | 11/1926 | Berger .......................... 606/113 |
| 1,772,352 | 8/1930 | Huber . |
| 3,791,387 | 2/1974 | Itoh . |
| 4,345,599 | 8/1982 | McCarrell .......................... 606/113 |
| 4,568,338 | 2/1986 | Todd . |
| 4,590,938 | 5/1986 | Segura et al. .......................... 606/127 |
| 4,694,838 | 9/1987 | Wijayarthna . |
| 4,738,667 | 4/1988 | Galloway . |
| 4,927,426 | 5/1990 | Dretler . |
| 5,071,649 | 12/1991 | Hunter . |
| 5,098,441 | 3/1992 | Wechler . |
| 5,108,420 | 4/1992 | Marks . |
| 5,171,233 | 12/1992 | Amplatz et al. . |
| 5,192,286 | 3/1993 | Phan et al. .......................... 606/110 |
| 5,290,229 | 3/1994 | Paskar . |
| 5,320,629 | 6/1994 | Noda et al. .......................... 606/113 |
| 5,330,482 | 7/1994 | Gibbs et al. . |
| 5,341,815 | 8/1994 | Cofone . |
| 5,342,371 | 8/1994 | Welter et al. . |
| 5,368,597 | 11/1994 | Pagedas .......................... 606/110 |
| 5,387,219 | 2/1995 | Rappe . |
| 5,486,182 | 1/1996 | Nakao et al. .......................... 606/110 |
| 5,522,819 | 6/1996 | Graves et al. .......................... 606/110 |
| 5,643,293 | 7/1997 | Kogasaka et al. .......................... 606/139 |

*Primary Examiner*—Robert A. Hafer
*Assistant Examiner*—Justine R. Yu
*Attorney, Agent, or Firm*—Nixon & Vanderhye P.C.

[57] ABSTRACT

A medical device especially adapted to remove biological material (e.g., fibrin sheath) from the distal end of a patient-internal catheter includes a tubular element, a central wire positioned within the tubular element and a snare wire attached at one end to the central wire so as to form an acute angle therewith, and at its other end to the tubular member. The snare wire includes a proximally extending segment which follows a course of about 360° about the distal end of the tubular member, and thus may be positioned adjacent the catheter's distal end. By effecting relative rotation between the central wire and the tubular member (for example, by rotating the central wire about its longitudinal axis while maintaining the tubular member stationary) will cause the snare wire segment to wrap around the catheter's distal end. Thereafter, manipulation of the device so as to advance the wrapped snare wire segment in a distal direction will strip the biological material from the distal end of the catheter.

6 Claims, 2 Drawing Sheets

DEVICES FOR REMOVING FIBRIN SHEATHS FROM CATHETERS

RELATED APPLICATIONS

This application is a divisional of U.S. patent application Ser. No. 08/417,018 filed on Apr. 5, 1995 (now U.S. Pat. No. 5,556,380) related to U.S. patent application Ser. No. 08/417,019 filed on Apr. 5, 1995 (now U.S. Pat. No. 5,643,281), the entire content of which is expressly incorporated hereinto by reference.

FIELD OF INVENTION

The present invention relates generally to the field of medical devices. More particularly, the present invention relates to the field of snares used during medical procedures to remove material from a patient. In its preferred embodiments, the present invention is especially adapted to remove fibrin sheaths from the distal ends of intravascular catheters.

BACKGROUND AND SUMMARY OF THE INVENTION

Catheters formed of a biocompatible plastics material are sometimes implanted in patients to relieve various symptoms and/or to assist in medical procedures. For example, central venous catheters have been implanted into a patient's vein during vascular surgery. One problem associated with such implanted catheters, however, is that a fibrin sheath (which is a deposit of fibrin and platelets) may form on the implanted catheter, initially at the entrance site into the vein and then along the length of the catheter. While it usually takes weeks to months for the fibrin sheath to form, it has been reported to form in as little as 24-48 hours following implant.

The fibrin sheath can cause catheter dysfunction, usually being manifested by the physician being able to infuse through, but not to aspirate from, the catheter. Intraluminal urokinase may then be administered several times to exclude the possibility of intraluminal clotting. If intraluminal urokinase treatment is ineffective, fluoroscopy may then be performed to allow the physician to evaluate catheter tip location and to obtain evidence of fibrin sheath formation.

Once the presence and extent of the fibrin sheath have been identified, the physician must take the necessary steps to remove the sheath from the implanted catheter. While it is conceivable that the implanted catheter may be removed and replaced surgically, it is more desirable for the fibrin sheath to be removed without surgical removal of the implanted catheter.

Presently, there are basically two approaches which may be employed without removal of the implanted catheter. The first approach involves introducing percutaneously a gooseneck snare (e.g., a snare device generally disclosed in U.S. Pat. No. 5,171,233 to Amplatz et al, the entire content of which is incorporated expressly hereinto by reference) into the patient's groin area. The snare is then advanced through the patient's femoral vein to the catheter implant site, at which time it is manipulated so that the snare encircles the distal end of the implanted catheter so that the fibrin sheath may be stripped therefrom. While the fibrin sheath which is stripped from the distal end of the implanted catheter travels to the patient's lung, surgical removal has been shown to result in embolization as well.

Another technique that has been employed to strip fibrin sheaths from the distal ends of implanted catheters is to introduce a J-tipped wire intraluminally through the implanted catheter. Rotation of the J-tipped wire about the distal end of the implanted catheter will thus strip a portion of the fibrin sheath therefrom. While this technique is advantageous since the implanted catheter serves as a guide passageway (i.e., separate incisions to access the femoral vein are unnecessary), the J-tipped wire is typically only capable of removing less than all of the fibrin sheath from the implanted catheter due to its size limitations.

What has been needed in this art, therefore, is a medical device which is capable of being guided intraluminally through an implanted catheter, but which is capable of removing substantially all of the fibrin sheath that may have formed at the catheter's distal end. It is towards fulfilling such a need that the present invention is directed.

Broadly, the present invention is embodied in medical devices having a snare loop for removing patient-internal biological material from an implanted catheter (e.g., a fibrin sheath which may form at the distal end of a venous catheter) which may be inserted intraluminally through the catheter during a medical procedure. The tubular member has a length sufficient to allow its distal end portion extend beyond the distal end of the patient-internal catheter. A central wire element is movably positioned within the elongate tubular member and has a sufficient length so that its terminal end portion extends distally beyond said distal end of said tubular member.

Importantly, a snare wire is provided such that one of its ends is attached to the central wire with the other end attached to the distal end of said tubular member after completing approximately 360° wrap around the tubular member between the ends. The snare wire, between its attached ends, will include a segment which extends proximally at an acute angle and may therefore be located upon manipulation of the device adjacent the distal end of the patient-internal catheter. Relative rotation between the central wire and the tubular member (e.g., by rotating the central wire about its longitudinal axis while maintaining the tubular member stationary or vice versa) causes said snare wire segment to be wrapped around said distal end of the patient-internal catheter. Distal advancement of this wrapped snare wire segment relative to said distal end of the patient-internal catheter will therefore strip the biological material therefrom.

Further aspects and advantages of this invention will become more clear after careful consideration is given to the following detailed description of the preferred exemplary embodiment thereof.

BRIEF DESCRIPTION OF THE DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
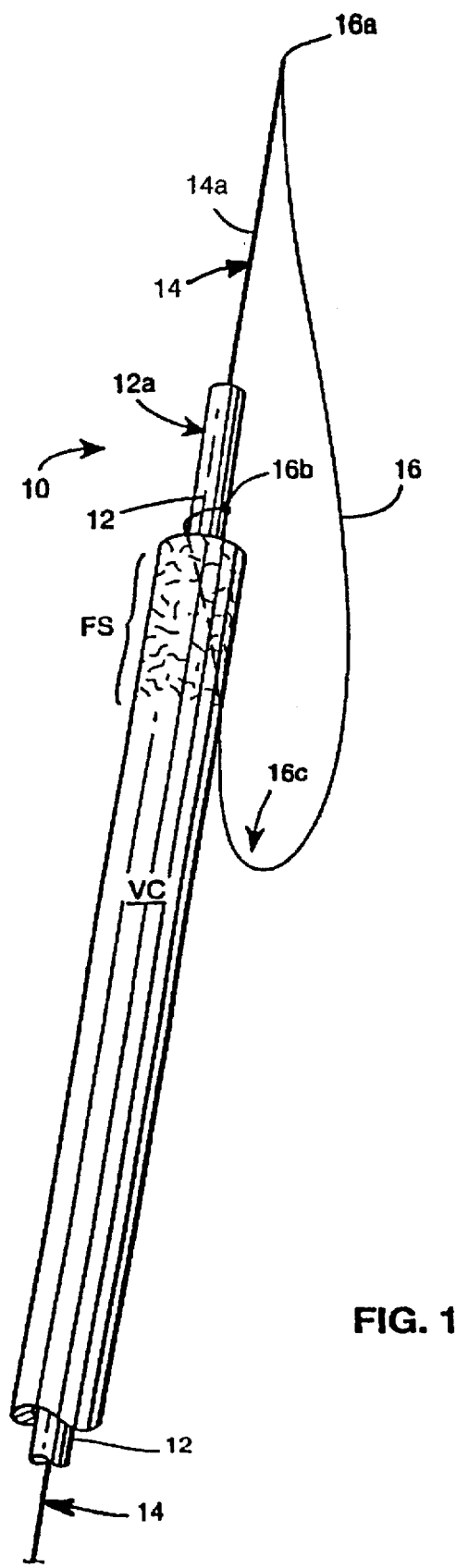
FIG. 1 is a schematic perspective view of a preferred medical snare device embodying the present invention.

One preferred embodiment of a medical snare device 10 according to the present invention is shown in accompanying FIG. 1. The snare device 10 is depicted schematically as being positioned intraluminally within a venous catheter VC, it being understood that the distal end region of venous catheter VC will in use be implanted within a patient's vein. The distal end section of the venous catheter VC is depicted in accompanying FIG. 1 as having a fibrin sheath FS extending proximally along the catheter's exterior surface.

The snare device 10 is generally comprised of an elongate tubular member 12 and a central wire element 14 which is movably positioned within the lumen of the tubular member 12. Each of the tubular member 12 and central wire element 14 is of sufficient length to allow the physician to intraluminally insert them as a unit through the venous catheter VC so that the distal end portion 12a of the tubular body 12 is capable of extending distally beyond the distal end of the venous catheter VC, and so that the terminal portion end 14a of the central wire element 14 is capable of being extended beyond the distal end portion 12a of the tubular member (e.g., to achieve relative positioning as shown in FIG. 1).

Important to the present invention, the snare device 10 includes a snare wire 16 formed of a flexible metal or plastics wire, thread or the like. The snare wire 16 has its distal end 16a physically attached to the central wire element 14 so as to form an acute angle therewith and its proximal end 16b physically attached (e.g., via biocompatible epoxy, heat-welding, imbedding or the like) to the tubular member 12 at or near its distal end 12a. The ends 16a, 16b are thus axially separated from one another along the length of the device 10 so as to form a snare loop collectively with the distal end portion 12a of the tubular member 12 and that length of the central wire element 14 extending therebeyond. As shown, the snare wire 16, between the ends 16a and 16b is preferably wrapped approximately 360° around the tubular member 12 so that the end 16b faces distally.

The relative diameters of the central wire 14 and the snare wire 16 are dependent in large part upon the particular medical procedure in which the device 10 of this invention is intended to be employed. It is preferred, however, that the diameters of the central wire 14 and the snare wire 16 each be within the range of about 0.001 to about 0.040 inch. Moreover, it is preferred that the snare wire 16 have a lesser diameter as compared to the central wire element 16 so that the former is relatively more flexible, while the latter is relatively more stiff. Therefore, it is preferred that the ratio of the central wire diameter to the snare wire diameter be between about 1.1:1 to about 10.0:1.

Figure 2A:
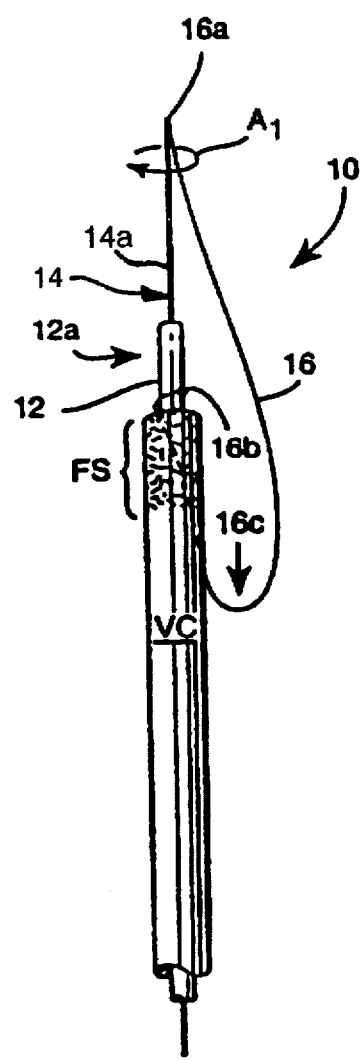
FIGS. 2A-2C are schematic elevational views showing a sequence of the device depicted in FIG. 1 during use.
Figure 2B:
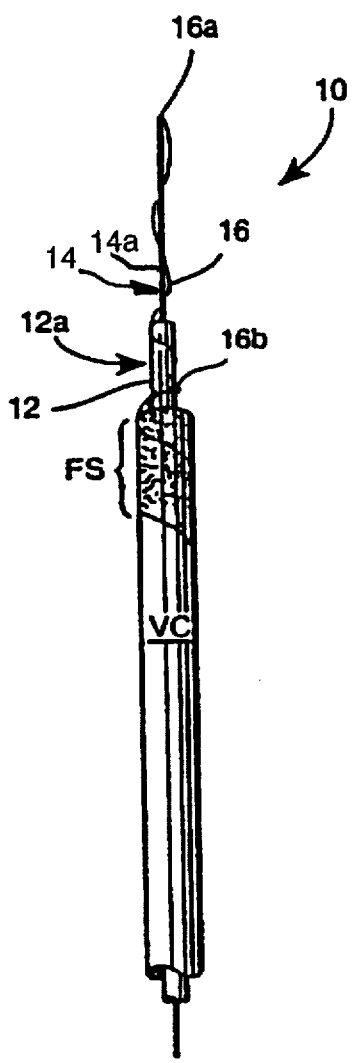
Figure 2C:
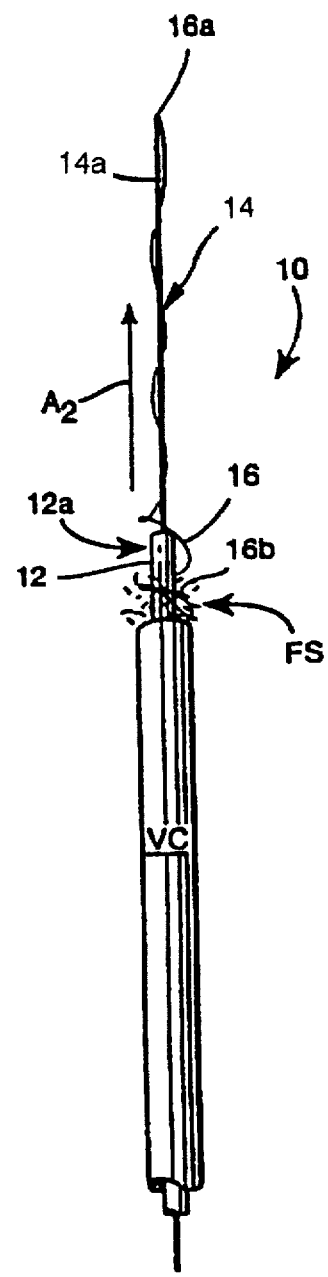

The snare wire 16 is of sufficient length between its ends 16a, 16b such that a segment 16c thereof may be positioned proximally of the end 16b adjacent the distal end of the venous catheter. With the snare wire segment 16c positioned in such a manner, the physician may rotate the central wire element 14 about its longitudinal axis within the lumen of the tubular member 12 as shown by arrow $A_1$ in FIG. 2A. Relative rotation between the central wire element 14 and the tubular member 12 (e.g., rotation of the central wire element 14 while maintaining the tubular member 12 stationary) will thereby cause the snare wire segment 16c to be wrapped or twisted more or less helically about the exterior surface of the venous catheter's distal end as shown in FIG. 2B. The several turns of the wrapped snare wire segment 16c will thus be brought into contact with the fibrin sheath FS at the distal end of the venous catheter VC. As such, advancement of the central wire 14 and/or the tubular member 12 in a distal direction (arrow $A_2$ in FIG. 2C) will, in turn, cause the wrapped snare wire segment 16c to be moved distally along the exterior surface of the distal end of the venous catheter VC thereby stripping the fibrin sheath FS therefrom.

The central wire element 14 may be provided with an eyelet (not shown) at its terminal end. However, it will be appreciated that the eyelet is not critically necessary since the end 16a of the snare wire 16 may be bonded to the central wire's terminal portion via biocompatible epoxy, solder, or the like, s depicted in the accompanying drawing FIGURES. Furthermore, the central wire 14 and the snare wire 16 may be formed as a single (unitary) monofilament wire, instead of the separate, but connected, wires as shown in the accompanying drawing FIGURES.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A medical device for removing biological material from a distal end of a patient-internal catheter comprising:

an elongate tubular member for intraluminal insertion within the patient-internal catheter and having a length sufficient to allow a distal end portion of said tubular member to extend beyond the distal end of the patient-internal catheter;

a central wire element positioned within said elongate tubular member and having a terminal end portion which extends distally beyond said distal end of said tubular member;

a snare wire having one end attached to said central wire element to form an acute angle therewith, and another end attached to said distal end of said tubular member at a position proximally of said one end of said snare wire which is attached to said central wire element; wherein said snare wire includes a segment between said one end and said another end thereof which follows a course which is wrapped about said tubular member and extends in a direction proximally of said another end of said snare wire so as to be located adjacent the distal end of the patient-internal catheter; and wherein said central wire and said tubular member are capable of relative rotation with respect to one another to cause said proximally extending snare wire segment to be wrapped around said distal end of the patient-internal catheter such that subsequent distal advancement of said wrapped snare wire segment relative to said distal end of the patient-internal catheter strips the biological material therefrom.

2. A medical device as in claim 1, wherein said segment of said snare wire follows a course so as to be wrapped about 360° around the tubular member.

3. A medical device as in claim 1, wherein said one end of said snare wire is bonded to a terminal end of said central wire element.

4. A medical device as in claim 1, wherein said central wire element and said snare wire are unitary with one another.

5. A medical device as in claim 1, wherein said central wire element and said snare wire each have a diameter between about 0.001 to about 0.040 inch.

6. A medical device as in claim 5, wherein a ratio of the central wire element diameter to the snare wire diameter is between about 1.1:1 to about 10.0:1.

* * * * *